(12) United States Patent
Lee (10) Patent No.: US 6,514,769 B2
(45) Date of Patent: Feb. 4, 2003

(54) MULTIPLE ANALYTE ASSAY DEVICE WITH SAMPLE INTEGRITY MONITORING SYSTEM

(76) Inventor: Jin Po Lee, 13150 Glen Cir., Poway, CA (US) 92064

( * ) Notice: Subject to any disclaimer, the term of this patent is extended or adjusted under 35 U.S.C. 154(b) by 0 days.

(21) Appl. No.: 09/364,277

(22) Filed: Jul. 29, 1999

(65) Prior Publication Data

US 2002/0001854 A1 Jan. 3, 2002

Related U.S. Application Data (63) Continuation-in-part of application No. PCT/US98/15369, filed on Jul. 22, 1998.

(51) Int. Cl.[7] ............................................. G01N 33/543
(52) U.S. Cl. ................ 436/518; 436/524; 436/538; 436/810; 435/7.1; 435/7.2; 435/174; 435/970; 435/971; 422/56; 422/58; 422/104; 422/110
(58) Field of Search ............................. 436/518, 524, 436/538, 810; 435/7.1, 7.2, 174, 970, 971; 422/56, 58, 104, 110

(56) References Cited

U.S. PATENT DOCUMENTS

| | | | |
|---|---|---|---|
| 4,056,359 A | | 11/1977 | Janin |
| 4,275,149 A | | 6/1981 | Litman et al. |
| 4,318,709 A | * | 3/1982 | Falb et al. |
| 4,518,565 A | * | 5/1985 | Boger et al. |
| 4,943,522 A | | 7/1990 | Eisinger et al. |
| 5,073,484 A | | 12/1991 | Swanson et al. |
| 5,096,833 A | | 3/1992 | Lau et al. |
| 5,143,694 A | | 9/1992 | Schafer et al. |
| 5,238,652 A | | 8/1993 | Sun et al. |
| 5,252,496 A | | 10/1993 | Kang et al. |
| 5,356,782 A | * | 10/1994 | Moorman et al. |
| 5,384,264 A | | 1/1995 | Chen et al. |
| 5,602,040 A | | 2/1997 | May et al. |
| 5,654,162 A | | 8/1997 | Guire et al. |
| 5,714,389 A | | 2/1998 | Charlton et al. |
| 5,770,458 A | * | 6/1998 | Klimov et al. |

FOREIGN PATENT DOCUMENTS

EP             0903584 A1  *  3/1999

* cited by examiner

Primary Examiner—Bao-Thuy L. Nguyen
(74) Attorney, Agent, or Firm—Stacy L. Taylor; Foley & Lardner (57) ABSTRACT

An assay device, a fluid analyte sample separator device and methods for use of thereof for determining whether the integrity of a fluid analyte sample has been compromised and for contemporaneously assaying the sample for the presence or absence of multiple analytes, such as drugs of abuse. The device is composed of a housing having separate slots therein for insertion of one or more analyte test strips, one end of which protrudes from the housing, and one or more units of a sample integrity monitoring system. The device may be used in dipstick or cassette form. An analyte sample separator for division of sample and retention of uncontaminated sample for further testing is also provided. The analyte test strips and sample integrity monitoring system are replaceable, so that the panel of analytes and of sample condition parameters tested can be customized.

22 Claims, 4 Drawing Sheets

MULTIPLE ANALYTE ASSAY DEVICE WITH SAMPLE INTEGRITY MONITORING SYSTEM

CROSS-REFERENCE TO RELATED PATENT APPLICATION

This is a continuation-in-part (for purposes of U.S. patent prosecution) of International Application No. PCT/US98/15369, filed Jul. 22, 1998, designating the United States, still pending.

FIELD OF THE INVENTION

The present invention relates to methods and devices for assaying biological fluid samples. More particularly, the invention relates to methods and devices for detecting multiple analytes in fluid sample while also determining whether the condition of the sample has been altered or degraded.

HISTORY OF THE RELATED ART

In their most simple form, chromatographic analyte analyte test strips permit an assay to be performed in a single step (application of an analyte sample to the device) to produce visually observable assay results (such as those indicated by colored bars on the analyte test strip). However, a common limitation of such analyte test strips is that they can only be used to detect a single analyte, requiring that serial assay procedures be performed to detect additional analytes (for example, to test a sample for the presence of a panel of narcotics). Multiple dipping steps, such as are commonly used when multiple dipstick assays are separately performed, present not only a possible loss of sensitivity of the assay (through reagent mixing or loss of reagent solutions), but also an esthetic and hygienic problem for the analyst. Repetitive performance of assay procedures is also tedious, which increases the risk that assays will be performed improperly or the results misinterpreted.

A further limitation on the accuracy of analyte assays is the potential for adulteration or degradation of the analyte sample prior to performance of the assay. This is an especially acute problem in assays for drugs of abuse in urine, where test subjects are often motivated to creatively alter the composition of the urine sample to produce falsely negative assay results.

SUMMARY OF THE INVENTION

The present invention provides an assay device, device for separating a fluid analyte sample for use in multiple assay procedures and methods for performing multiple analyte assays while contemporaneously evaluating whether the analyte sample has been adulterated or otherwise compromised.

To the latter end, the invention provides assay devices which include an assay sample integrity monitoring system. The system consists of a pad in which determinants are provided which allow for measurement of parameters indicative of the condition of a fluid analyte sample, such as specific gravity and pH. The pad is in fluid communication with a carrier membrane, through which analyte sample flows without contacting the analyte analyte test strips of the device.

Analyte sample fluid is added to the device and becomes divided between the carrier membrane and the analyte test strips, thus allowing for contemporaneous measurement of both analytes and adulterants or other compromising elements in the analyte sample. The separation of the analyte sample between the carrier membrane and the analyte test strips avoids the possibility of contamination of the sample by analyte test strip reagents which might affect the sample integrity determination.

In one embodiment of the assay device, the assay device is a dipstick having multiple analyte test strips, each of which includes a test zone and a control zone. The analyte test strips are enclosed in a housing having an open side through which an end of each analyte test strip protrudes to form a sample loading zone. A protective cap is provided to seal the protruding ends of the analyte test strips from exposure while not in use. Each analyte test strip is separated from the next within the housing by a raised spacer. The portion of the housing which overlies the test and control zones is transparent to permit visually observable results shown in each zone to be viewed.

In cassette form, the assay device has the same structure described above, but the protruding analyte test strips are inserted into a cap which has a sample port for application of sample to the analyte test strips. The cap is retained on the assay device by a close fit over the device housing.

In either its dipstick or cassette form, the sample integrity monitoring system works in parallel with the analyte test strips of the devices of the invention. In particular, the carrier membrane can occupy the same slot in the device base as the analyte test strip, and will include a fluid migration barrier between the analyte test strip and the integrity determinant pad, or can occupy separate slots in the base.

Each analyte test strip provides binders and assay reagents for detection of a different analyte in the sample fluid. In a particularly preferred embodiment of the assay device, the housing may be opened to permit substitution of different analyte test strips to allow each device to be customized for detection of specific analytes of interest.

The invention also provides a separator device for dividing a fluid assay analyte sample into portions for use in multiple assays without need for contact between the assay operator and the fluid sample. This latter feature of the device increases operator safety and avoids inadvertent contamination of the assay sample. The separator device may be used to separate any fluid assay sample, but is especially useful in assaying samples for the presence of narcotics, where a positive result on first testing of the sample may necessarily be followed by additional testing of the sample to confirm the result and the identity of the detected narcotic. To this end, the separator device is adapted particularly well to use with the assay device of this invention.

The assay device of the invention makes specimen analysis easier and increases its accuracy because an analyte sample need only to be applied once to the assay device for testing and can, in the same step, be evaluated for potential adulteration or compromise. In addition, the replaceable nature of the analyte test strips and integrity monitoring system allows the analyst to customize the array of assays and integrity monitoring system determinants to the testing situation. Because the customization can be performed before adding the test sample (e.g., urine), fewer manipulations with the analyte sample are needed to obtain the desired information. In addition, use of the separator device permits further testing of the sample to be performed without risk of adulterating the sample in a preliminary assay performed according to the invention.

The invention also provides a method for assaying one or more analytes of interest. The protruding ends of the device are dipped into a fluid analyte sample. Binding of an analyte present in the sample with one or more specific ligands causes formation of specific visual pattern in the test and control zones indicative of the test result. In addition, passage of the sample into the sample integrity monitoring system also produced visual results (which vary depending on the parameters evaluated), thereby enabling the assay operator to immediately determine whether the sample appears to be adulterated or otherwise compromised.

The assay results performed according to the invention may be read visually without use of separate measuring equipment. Thus, performance of assays according to the invention requires only that the user introduce the requisite amount of test sample into the device of the invention, then observe any color changes which appear shortly thereafter in a detection zone of an analyte strip. The method of the invention is especially useful for screening fluid analyte samples (e.g., urine) for the presence or absence of drugs of abuse.

BRIEF DESCRIPTION OF THE DRAWINGS

FIG. 3B is a top view of the lower half, base portion of the sample port cap, while

Like numerals refer to like elements in the drawings.

DETAILED DESCRIPTION OF INVENTION

A. Definitions

For ease of understanding, the following definitions will apply throughout this description:

1. The term "antigen" as used herein refers to any analyte which is capable of binding antibodies. Antigens may comprise, without limitation, chemical compounds, polypeptides, carbohydrates, nucleic acids, lipids, and the like, including viral particles, viral subunits, bacterial and parasite surface antigens, and host proteins that may be diagnostic of the subject's condition.

2. A "binder" refers to a ligand for the analyte as in the format of a sandwich assay, or a ligand for both the analyte and the tracer as in the format of a competitive assay. A binder can be chosen from a group of molecules or compounds capable of binding the analyte, such as an antigen to the antibody analyte, or an antibody to the antigen analyte.

3. A "test zone" refers to an area in which a binder or the analyte is attached, movably or immovably, to the analyte test strip portion of an assay device.

4. A "tracer" refers to a ligand for the analyte or the binder labeled with a detectable label, preferably a visually readable particulate label, such as colloidal gold, latex and liposomes including dye, carbon black, and the like.

5. A "sample loading zone" refers to an area of a analyte test strip on which a fluid analyte sample is applied for migration to the test zone.

6. A "analyte test strip" of the invention consists of, collectively, all of the zone supporting membranes and any filters of the assay device.

7. A "fluid analyte sample" can be any fluid suspected of containing analyte of interest for which a particular assay is specific. Test sample may represent any body fluid, including urine, blood, sweat, lymph, intraperitoneal fluid, crude tissue extract or homogenate, derived from a fetus, neonate, juvenile or adult subject; a non-biological fluid such as water from some ecological niche, e.g., a river or a lake; or a solution used in a laboratory.

8. A "label" is a molecule or compound which directly or indirectly mediates the formation of a signal (such as a color change) which is used in assay to indicate the presence, absence or concentration range of analyte of interest in a test sample. Labels may include enzymes, fluorescers, liposomes, erythrocyte ghosts, polymer microcapsules, color polymer particles (latex), and preferably includes sols of metal-containing compounds. A wide variety of patents and patent applications provide an extensive literature of different techniques for producing detectible signals in immunoassays. The following list of United States patents is merely illustrative of the type of label which can find application in this invention: U.S. Pat. No. 3,646,346 discloses radioactive label; U.S. Pat. Nos. 3,654,090, 3,791, 932, and 3,817,838 disclose enzyme labels; U.S. Pat. No. 3,996,345 discloses fluorescer-quencher labels; U.S. Pat. No. 4,062,733 discloses radioactive label; U.S. Pat. No. 4,067,959 discloses fluorescer or enzyme label; U.S. Pat. No. 4,104,099 discloses chemiluminescent label; and U.S. Pat. No. 4,160,645 discloses non-enzymatic catalyst label. U.S. Pat. No. 3,966,879 discloses an electrophoretic technique employing an antibody zone and U.S. Pat. No. 4,120, 945 discloses a radioimmune assay (RIA) where labeled analyte is initially bound to a solid support through antibody. U.S. Pat. No. 4,233,402 discloses enzyme pair labels; U.S. Pat. No. 4,720,450 discloses chemically induced fluorescent labels; and U.S. Pat. No. 4,287,300 discloses enzyme anionic charge labels.

Labels can also be metal-containing sols; i.e., metal or metal compounds such as metal oxides, metal hydroxides, metal salts, metals or metal-containing compounds mixed with polymers or coated onto polymer nuclei. These metal labels may include dry forms of any of the above-named metal or metal compound sols, and preferably includes colloidal gold in dry form.

9. A "complex" means (depending on the context) any multimolecular complex formed by analyte and one or more ligands, or by labeled ligand and immobilized ligand. In a sandwich-type immunoassay, e.g., the following complexes occur: analyte/labeled ligand duplex first produced in the assay (first complex) and analyte/labeled ligand/ immobilized ligand triplex formed second in the assay (second complex).

10. "Fluid communication" refers to structures which are in contact with, but not necessarily affixed to, one another.

11. "Assay" refers to several different types of assay formats in which an analyte of interest can be detected using an assay analyte test strip. For example, in a sandwich-type immunoassay, analytes of interest in the analyte sample, when present, bind a labeled tracer movably incorporated in the analyte test strip (consisting of a porous membrane) at the tracer zone to form a first complex. The tracer is a molecule which binds the analyte of interest and is conjugated to a label, preferably a metal label, and most preferably colloidal gold.

A second immobilized ligand corresponding to the analyte of interest is coupled to the analyte test strip at the test zone. First complex and unbound labeled ligand mix with the test sample and be carried along therewith by capillary action (wicking) through the test zone. Analyte sample passes through the analyte test strip bringing the first complexes, if any, into contact with the unlabeled ligand immobilized in the test zone to form a second complex of labeled ligand-analyte-immobilized ligand. The first immobilized ligand is immobilized in the test zone by means known in the art, including covalent bonding or attachment to an insoluble protein-coated surface (see, e.g., U.S. Pat. Nos. 4,200,690 and 5,075,078). When the second complex is formed, a visible color pattern appears in the test zone. Labeled ligand not bound to analyte in the test sample continue migration by wicking into the control zone to contact the ligand immobilized there. The labeled ligand can bind the immobilized ligand in the control zone to form a third complex, and thus be captured in the control zone.

Within the scope of this invention, the labeled ligand forming the complex in the control zone may be the same as the tracer forming the first and second complexes, or it may be a different labeled ligand. The ligand immobilized in the control zone should have specific affinity for the labeled ligand intended to form the third complex. Formation of the third complex is indicated by a visible pattern in the control zone.

Besides sandwich immunoassay method, other assay methods may be implemented in the devices of the invention. These methods may include competition and inhibition assays. In a competition assay, the analyte and tracer have similar affinity properties and compete for binding with immobilized ligand. Thus, in absence of analyte, the pattern (e.g., band) in the test zone is of maximum intensity. When present, the analyte binds to immobilized ligand to prevent the tracer from getting captured in the test zone. Thus, the intensity of the test band is reduced, depending on the concentration of analyte in the test sample.

In an inhibition assay, the analyte and immobilized ligand in the test zone each have affinity for the tracer. In the absence of analyte in the analyte sample, the tracer is captured by immobilized ligand, and a visible pattern forms in the test zone. When present, the analyte binds the tracer, thereby preventing it from binding to the immobilized ligand in the test zone. The resulting intensity of the test band is reduced depending on the concentration of analyte in the test sample.

12. The term "sample integrity monitoring system" refers to one or more strips on which a determinant indicative of conditions in a fluid sample are provided. The system is generally provided as an integral part of an assay device of the invention, in fluid communication with the analyte test strips.

B. Assay System of the Invention

1. Analyte Test Strips and Sample Integrity Monitoring System

Subjects undergoing drug tests are sometimes creative in their efforts to adulterate the analyte samples to evade detection of drugs of abuse likely to be present in the sample. To minimize the effects of such evasion efforts on results obtainable with the assay devices of the invention, the invention provides a sample integrity monitoring system which determines whether adulterants have been added to the sample or if its quality is otherwise compromised. For example, the sample integrity monitoring system of the invention may evaulate any or all of the pH, osmolality (the total concentration of solutes in urine, expressed as mOsm/kg and measured as a function of fluid specific gravity) of, or albumin, creatinine, glutaraldehye and nitrite levels in, the sample.

Figure 1:
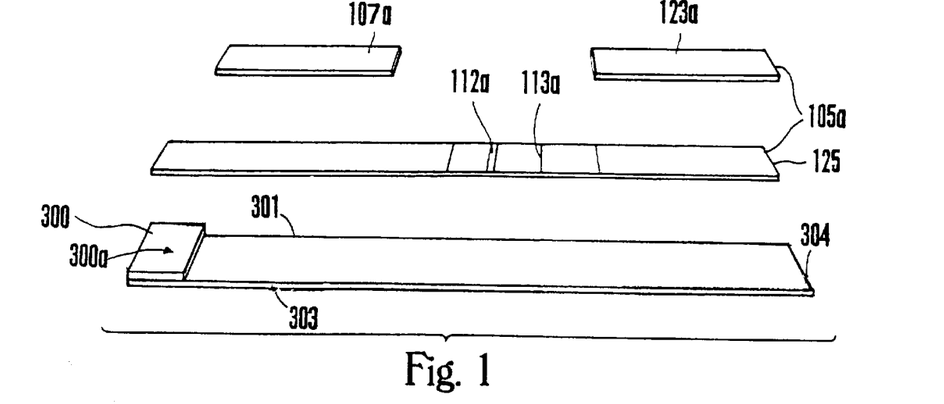
FIG. 1 is an exploded view of a dipstick assay device of the invention.
Figure 2:
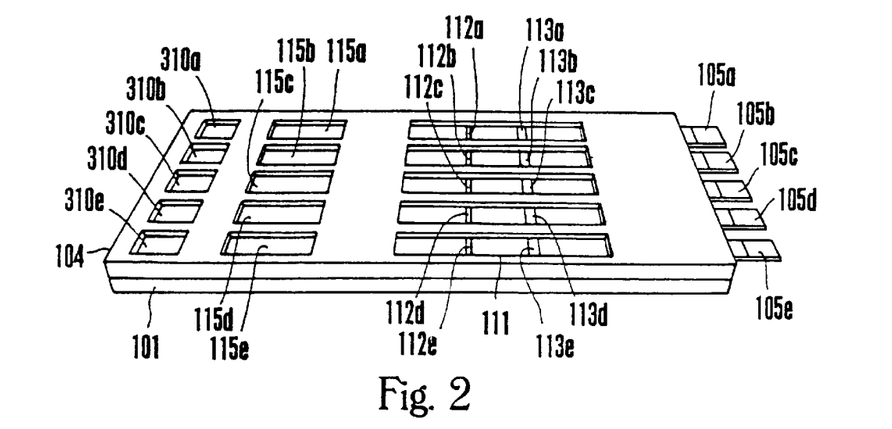
FIG. 2 is a top view of a dipstick assay device of the invention.

Turning to FIG. 1, an embodiment of the sample integrity monitoring system is shown in exploded view. This description is made with specific reference to a single analyte test strip (105A); however, it will be understood that the sample integrity monitoring system may also be used in an assay device with multiple analyte test strips (e.g., as shown in FIG. 2 and FIG. 3).

The sample integrity monitoring system consists principally of integrity determinant pad 300. Integrity determinant pad 300 is formed of a bibulous membrane into which a determinant (described in greater detail below) is incorporated on or through surface 300A of integrity determinant pad 300. As shown in FIG. 1, integrity determinant pad 300 rests in the plane above analyte test strip 105A; however, pad 300 is not in appreciable fluid communication with analyte test strip 105A. In this respect, by "not in appreciable fluid communication", it is meant that very little of the analyte sample fluid which has been carried through analyte test strip 105A, and has contacted the analyte test reagents therein, comes into contact with integrity determinant pad 300.

More particularly, integrity determinant pad 300 rests on carrier membrane 303. Carrier membrane 303 is parallel with, and underlies, analyte test strip 105A. On one hand, carrier membrane 303 extends beyond the downstream end of analyte test strip 105A to form a platform on which integrity determinant pad 300 rests. Fluid communication between integrity determinant pad 300 and analyte test strip 105A is prevented by fluid barrier zone 301.

Fluid barrier zone 301 is formed of any convenient means for stopping the migration of fluid from analyte test strip 105A to integrity determinant pad 300 including, without limitation, a physical gap between the downstream end 125 of analyte test strip 105A and integrity determinant pad 300, a hydrophobic film disposed on carrier membrane 303 between the downstream end of analyte test strip 105A and integrity determinant pad 300 and an absorbent pad between the downstream end of analyte test strip 105A and integrity determinant pad 300, which absorbent pad may also be imbued with a hyrophobic material. Those of ordinary skill in the art will be familiar with, or may readily ascertain, the identity of hydrophobic films and other materials suitable for use in analyte test strips.

Thus, analyte sample fluid which has not passed through analyte test strip 105A is brought instead into contact with integrity determinant pad 300 via passage through carrier membrane 303. Carrier membrane 303 is physically separated from analyte test strip 105A by a layer of non-bibulous paper 304. In alternative embodiments paper 304 may be replaced by a porous membrane, a non-porous membrane or eliminated; however, a non-bibulous and/or hydrophobic barrier between carrier membrane 303 and analyte test strip 105A is desirable to assist in dividing portions of the analyte sample fluid between the two layers. With such division, analyte sample fluid reaching integrity determinant pad 300 will be free of contamination with reagents which may be released from test zone 112 or control zone 113, thereby eliminating the possibility of interference by any such reagents with the sample integrity determination.

Carrier membrane 300 is typically constructed of material which is substantially inert with respect to the analyte and must be porous or absorbent relative to the analyte sample to be tested, e.g., urine, and must maintain their structural integrity when exposed to aqueous solutions or physiological fluids. Bibulous matrices that can be useful for the devices of the present invention include but are not limited to, paper, sponge materials, cellulose, hydrophilic inorganic powders, wood, synthetic resin fleeces, woven and non-woven fabrics and like materials.

Nonlimiting examples of nonbibulous matrices include glass fiber, permeable polymer films and preformed or microporous membranes. The absorbent material is preferably absorbent paper. The absorbent material can be affixed by a double sided adhesive (e.g., two sided adhesive tape) to a solid moisture impervious support. This support can be constructed from, for example, hydrophobic plastic, cellulose acetate, polyethylene, terephthalate, polycarbonate, or polystyrene.

The analyte test strips are conventional in form, therefore, because those of ordinary skill in the art will be abundantly familiar with the design of such analyte test strips, they will not be described in detail here. However, each analyte test strip will have a test zone 112 for binding of analyte (to indicate a positive test result for the presence of analyte in the analyte sample) and a control zone 113 for binding of tracer (to indicate correct operation of the assay). Preferably, the test zones and control zones of each analyte test strip lie in the same location on each analyte test strip so each can be viewed in side-by-side fashion. A sample loading zone 123A (e.g., an absorbent pad or bibulous membrane) will comprise the upstream end of each analyte test strip (as, for example, 123A, 123B, 123C, 123D and 123E of FIG. 313), which loading zone will be in fluid communication with test zones 112 and 113. A label 107A (FIG. 1) may also be present on each test strip. The labels may be printed with information (not shown) of use in performing the assay, such as the identity of analyte detectable with each analyte test strip.

The tracer is prepared according to the means known in the art. For purposes of producing a clearly visible reaction, labels of metal-containing sols are preferred, with labels of colloidal gold or selenium being most preferred. An example of a suitable product is colloidal gold available from Janssen Life Sciences Products. These colloidal metals produce distinctive visual patterns without addition of further reagents; however, fluorescers (such as fluorescein) and enzymes (such as those identified in U.S. Pat. No. 4,275, 149), may also be used.

Selections and choices for test binders (e.g., immobilized antigens, antibodies and other test and control binders), as well as suitable means for their attachment to porous analyte test strip membranes, are well-known to those of ordinary skill in the art and will not be stated in detail here. To maximize contact of test sample with the tracer and all test binders, the area occupied by each reagent on the analyte test strip preferably extends from one side of the membrane to the other.

For further review concerning analyte test strip construction, including selection and preparation of test reagents, the following references provide a representative sample of analyte test strip designs known in the art: U.S. Pat. No. 5,384,264 (commonly owned); U.S. Pat. Nos. 4,491,645; 4,943,522; 5,252,496; 5,714,389 and 5,602,040, the disclosures of which are incorporated for purposes of reference.

Specific examples of test means (e.g., reagents reactive with adulterating components) for use in determining specific values which reflect the integrity of urine samples are noted below. In view of the creativity which often accompanies efforts toward adulteration of samples for drug assays, new reagent sets are frequently developed for use in assaying for the presence of such adulterants as they come into use. Thus, those particular test means described herein should be regarded as merely representative of test means which could be utilized in the invention. Those of ordinary skill in the art will be familiar with, or can readily ascertain, the identity of other means for use in determining the integrity of urine and other fluid samples.

In each case, however, the test means provide a detectable signal, preferably a visually detectable signal, indicative of adulteration, or the absence thereof, in the analyte sample fluid. In general, such detectable signal will be provided by interaction (e.g., binding) between determinants incorporated in integrity determinant pad 300 (so as to be detectable from surface 300A thereof) and specific adulterants present in the analyte sample fluid.

Where the integrity monitoring system determines the pH of the test sample, sample integrity determinant pad 300 is impregnated with various dyes that respond with different color changes to a pH in the range of 5 to 9. Depending on the acid-base status, urinary pH may range from as low as 4.5 to as high as 8.0. Although this test is done routinely, it neither identifies nor excludes patients with urinary system disease. The test can, however, indicate that the condition of the urine sample has deteriorated.

Where the integrity monitoring system determines the specific gravity (which is directly proportional to urine osmolality) of the test sample, integrity determinant pad 300 is modified to measure specific gravity in approximations. For example, U.S. Pat. No. 4,318,709, to Falb et al., provides a test means for determining the ionic strength or specific gravity of an aqueous test sample, the test means comprising a weakly acidic or weakly basic polyelectrolyte which is at least partially neutralized, and an indicator means capable of producing a detectable response to ion exchange between the polyelectrolyte and the sample. The test device is a carrier matrix incorporated with the test means, and the method for its use involves contacting an aqueous test sample with the device and observing a detectable response. The disclosure of the '709 Patent is incorporated for reference herein; its teachings can be adapted to modify integrity determinant pad 300 to serve as the carrier matrix into which the test means will be incorporated.

Normal urine osmolality varies between 50 and 1200 mOsm/kg (specific gravity between 1.002 and 1.035). Any urine having a specific gravity over 1.035 is either contaminated, contains very high levels of glucose, or the patient may have recently received high density radiopaque dyes intravenously for radiographic studies or low molecular weight dextran solutions.

Commercially available analyte test strips also permit simple and rapid testing for protein. Methods based on dye binding techniques have proven especially useful because dye binding methods are readily automated and provide reproducible and accurate results. In general, dye binding techniques use pH indicator dyes that are capable of interacting with a protein, such as albumin, and that are capable of changing color upon interaction with a protein absent any change in pH. When a pH indicator dye interacts with, or binds to, a protein, the apparent pKa (acid dissociation constant) of the indicator dye is altered and the dye undergoes a color transition, producing the so-called "protein-error" phenomenon.

In methods utilizing the dye binding technique, an appropriate buffer maintains the pH indicator even at a constant pH to prevent a color transition of the pH indicator dye due to a substantial shift in pH. Due to the "protein-error" phenomena, upon interaction with the protein, the pH indicator dyes undergoes a color transition that is identical to the color change arising because of a change in the pH. Examples of pH indicator dyes used in the dry phase assay of proteins that are capable of interacting with or binding to proteins and exhibiting "protein-error" color transitions include tetrabromophenol blue and tetrachlorophenol-3,4,5, 6-tetrabromo-sulfophthalein. Simple, accurate and inexpensive protein detection assays have been developed for the detection or measurement of protein in urine and serum (see, e.g., U.S. Pat. No. 5,096,833 to Lau et al., incorporated herein for reference).

2. Assay Device Formats

Figure 3A:
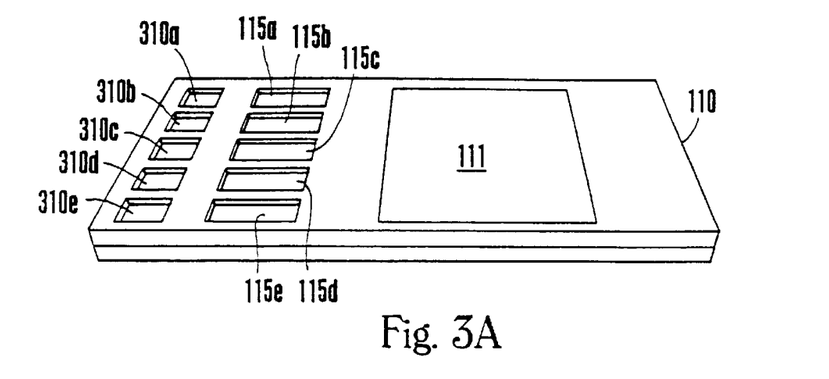
FIG. 3A is a top view of the upper half sample port cap of a cassette assay device of the invention.
Figure 3B:
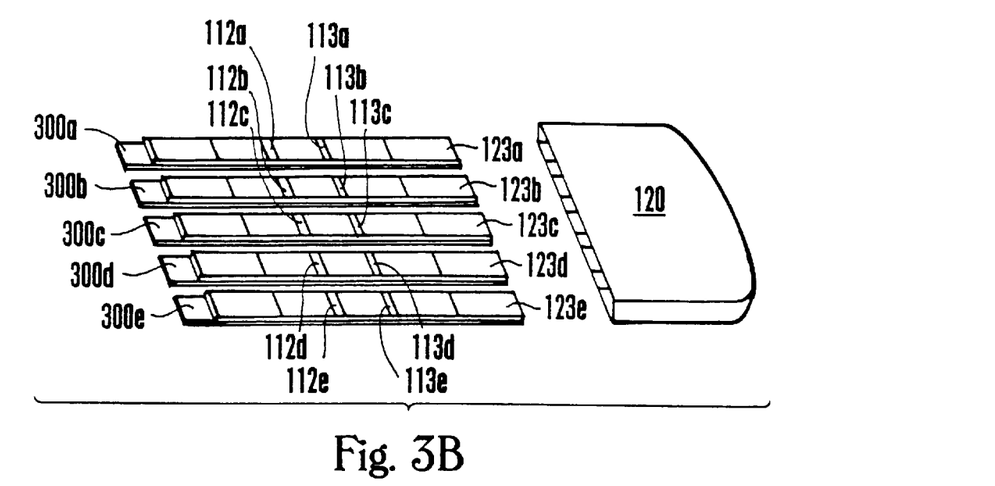
Figure 3C:
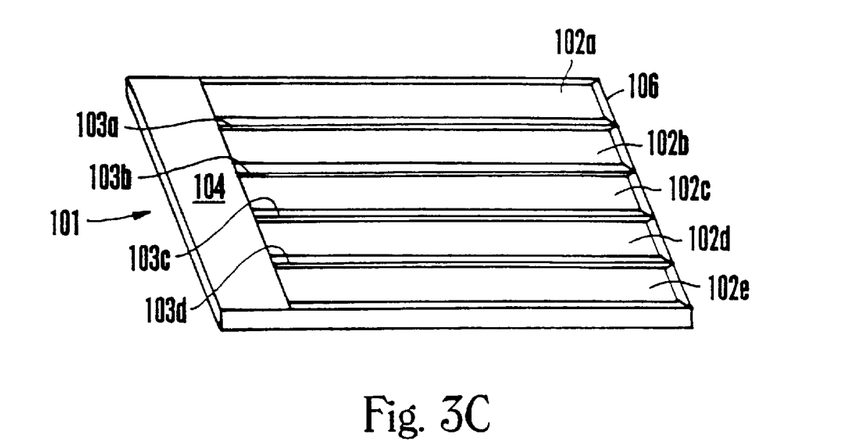
FIG. 3C is a side, cut-away view of the intact cap with analyte test strips in place therein.

Tuning to FIG. 3, a preferred dipstick device for use with the assay system of the invention is shown in exploded view. The device consists of a housing 100, which is defined by base 101 (FIG. 3C) and cover 110 (FIG. 3A). Base 101 can be constructed of any sterilizable material, such as a non-porous plastic (e.g., the commercially available plastic "ABS" supplied by the Monsanto Company of St. Louis, MO.). Referring to FIG. 3C, base 101 having a closed end 104 and an open end 106, slots 102A, 102B, 102C, 102D and 102E separated by rails 103A, 103B, 103C and 103D for insertion of analyte test strips (labeled in FIG. 2 as 105A, 105B, 105C, 105D and 105E). A particular advantage of this embodiment of the assay device is its customizability in that analyte test strips specific for different analytes of interest to the user may be inserted into base 101 and that the number of analyte test strips employed may vary (e.g., base 101 may have any number of slots from two upward to accommodate as many analyte test strips as the user may desire).

Conveniently, cover 110 (FIG. 3A) is also provided with transparent windows 115A, 115B, 115C, 115D and 115E through which labels on analyte test strips (labeled in FIG. 2 as 105A, 105B, 105C, 105D and 105E) can be viewed. Cap 120 (FIG. 3B) may also be provided to protect the protruding ends of analyte test strips (labeled in FIG. 2 as 105A, 105B, 105C, 105D and 105E) from contamination.

Referring to FIG. 2, when the sample integrity monitoring system of the invention is contained in an assay device housing 110, the housing will include transparent windows 310A, 310B, 310C, 310D and 310E through which surface 300A of integrity determinant pad 300 may be viewed. Those of ordinary skill in the art will recognize that, while the physical relationship of the sample integrity monitoring system to the analyte test strips of the devices described above is a convenient and efficacious one, other configurations may also be utilized in the invention. For example, integrity determinant pad 300 could be placed beneath carrier membrane 303. In such an embodiment, a window would conveniently be located in base 101 near closed end 104 so as to permit viewing of outer surface 300A of integrity determinant pad 300 through base 101. Alternatively, the analyte test strips of the device and the carrier membranes 303 on which integrity determinant pad 300 rest may occupy separate slots in base 101.

When inserted into slots 102A, 102B, 102C, 102D and 102E, the analyte test strips extend out of base 101 beyond open end 106. For use as a dipstick assay device, the length to which the analyte test strips protrude from base 101 must be sufficient to allow the analyte test strips to contact a fluid analyte sample, preferably by immersion, and most preferably without allowing the fluid to contact housing 100.

In some instances (e.g., where the analyte sample is believed to contain pathogenic organisms) it is desirable to protect the assay operator from contact with analyte sample after its application to an assay device. To this end, the dipstick assay device may be conveniently modified for use in closed cassette form.

Figure 4A:
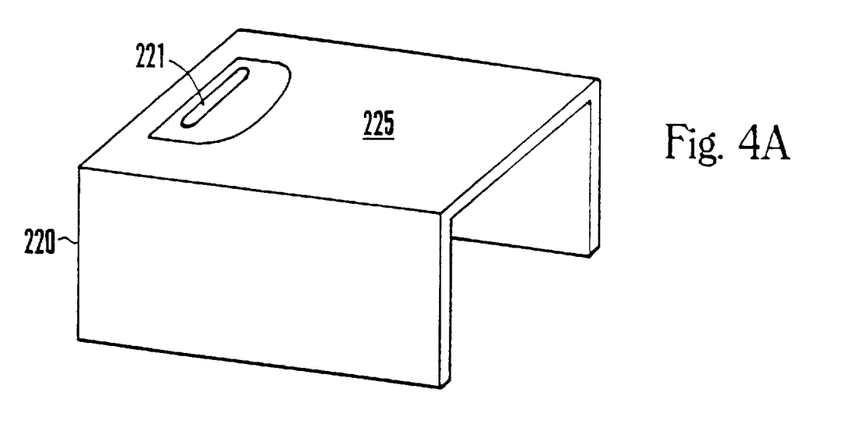
FIGS. 4A–4C is an exploded side view of an assay device of the invention showing the spatial relationship of the sample integrity monitoring system of the device to the analyte test strips of the device.
Figure 4B:
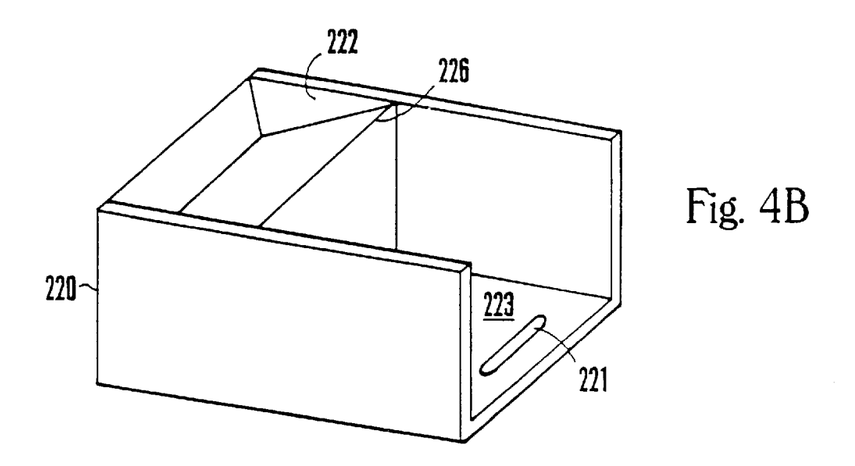
Figure 4C:
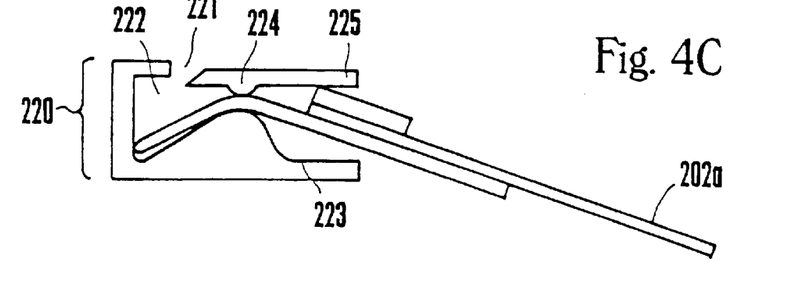

More specifically, cap 220 (FIGS. 4A and 4B) is adapted to convert the dipstick assay device into a cassette. Cap 220 has sample application slot 221 formed therein to permit analyte sample to be applied to analyte test strips dropwise; e.g., by pipetting the sample through slot 221 (in FIG. 4C, only strip 202A is visible from the side view and the device housing is not shown). To avoid sample overflow, a reservoir 222 may be provided in the inner floor 223 of cap 220 by, for example, providing raised bar 226 on floor 223 (in FIGS. 4A and 4B, floor 223 is shown as if split from roof 225 of the cap only for the purpose of permitting reservoir 222 to be viewed in the drawing). A downwardly protruding bar 224 is provided from the inner surface of roof 225 of cap 220 to depress the analyte test strips into reservoir 222 so each analyte test strip has equal access to the analyte sample. After performance of the assay, cap 220 remains in place on the assay device to protect the protruding ends of the analyte test strips from contact with other materials, from desiccation and from contact with the assay operator.

C. Separator Device for Division of Analyte Sample

If a positive result is obtained from use of the assay device of the invention, it is usually necessary to further characterize the detected compound to better enable its identification; e.g., by mass spectrometry. However, it is rarely practical to ask that more than one assay sample be obtained from a subject. As such, any assay sample which is obtained must be divided into portions of sufficient volume for repeated testing, for example by pouring the original sample into separate specimen containers (at the risk of operator contamination and sample loss). Even where the sample is only to be assayed once, the tendency of subjects to provide abundant urine samples poses a different problem in that too much sample can saturate a analyte test strip and overwhelm the assay reagents. Again, division of the sample is required.

The separator device of the invention provides simple means for dividing a sample while protecting the sample from contamination and the operator from the sample. To these ends, the separator device consists of a ring which is just smaller in diameter than the inner diameter of the open end of a specimen collection cup so, when pressed inside of the open end of the cup, the ring will remain seated there. A collection chamber (for example, a "V" shaped well) extends across the ring and is attached thereto so the ends of the collection chamber are closed by the inner walls of the ring.

In use, an assay fluid is placed within the specimen collection cup to a level below the point where the separator device will be seated. The assay operator presses the separator device into place and seals the specimen collection cup with a cap. The operator inverts the specimen collection cup several times so fluid pours into the collection chamber of the separator device. The balance of the fluid assay remains below the level of the separator device and is therefore protected from contact with reagents or other material placed therein. A analyte test strip (such as the assay device of the invention) is placed into contact with the portion of the assay sample contained within the collection chamber of the separator device; e.g., by dipping an end of the analyte test strip into the collection chamber. After the assay sample is loaded from the collection chamber onto the analyte test strip, the latter is removed and the separator device is carefully lifted from the specimen collection cup for disposal.

Use of the separator device provides the assay operator with a volume of assay sample fluid which is sufficiently limited to avoid saturation of the analyte test strip. For example, where the assay device utilized is the device of this invention, the collection chamber is of a depth and length sufficiently limited so the maximum fluid level achievable in the collection chamber is lower than the level of the assay device housing. The uncontaminated balance of the assay sample still in the specimen collection cup is available for further testing; e.g., for mass spectrometry to determine the identity of any compounds detected in the initial assay of the portion of the sample separated in the separator device.

Conveniently, the separator device may be provided in the form of a kit, including the separator device, a sterilized specimen collection cup with cap and forceps for removal of the separator device from the cup after performance of the assay. Such a kit may also be provided with the assay device of the invention.

Figure 5:
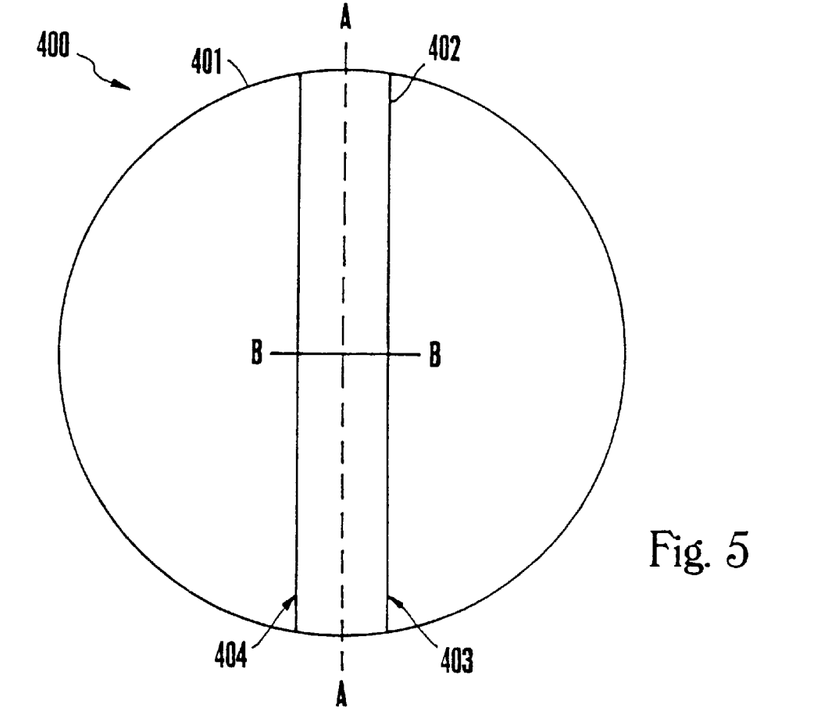
FIG. 5 is a top view of a separator device of the invention.
Figure 6:
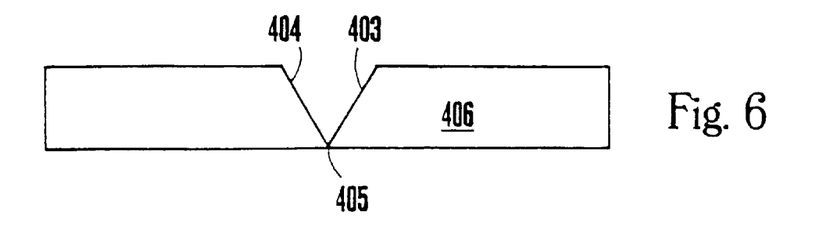
FIG. 6 is a cross-sectional view of the separator device taken along line A—A at cut-away point B—B of FIG. 5.

An example of a separator device is shown in FIG. 5 and FIG. 6. Although the separator device shown is in the shape of a ring (to correspond to the common cup-like shape of urine collection cups), those of ordinary skill in the art will recognize that the separator device may be of any shape which conforms to a specimen collection container having at least one open end into which the separator device may be seated.

Referring to FIG. 5, a top view of separator device 400 is provided. Ring 401 has an OD of slightly less than the ID of the specimen collection cup into which the separator device is to be placed. Collection chamber 402 spans ring 401 and is defined by walls 403 and 404.

Looking through separator device 400 along line A—A from cut-away point B—B (FIG. 6), it is seen that walls 403 and 404 meet at point 405 to form a V-shaped well. Those of ordinary skill in the art will recognize that collection chamber 402 may take the form of a half-circular, squared or other shaped well, but a V-shape is a convenient well form to manufacture. Collection chamber 402 is closed at both ends of the well by inner surface 406 of ring 401. Also, it will be appreciated that separator device 400 may be provided with more than one collection chamber.

When separator device 400 in place within specimen collection cup 410, the height of ring 401 is restricted so neither it nor collection chamber 402 extend above the level of the open mouth 411 of cup 410 (to avoid interfering with closure of cup 410 by its cap [not shown]). Assay sample fluid 412 remains below separator device 400 in cup 410.

Separator device 400 may be constructed of any sterilizable material which is acceptable for use with fluid assay samples, the identity of which will be known to those of ordinary skill in the art (e.g., plastics such as polycarbonate and glass). Preferably, the material will be non-porous and hydrophobic.

D. Methods for Use of the Assay Devices

The method of the invention may be used to detect any analyte present in fluid sample. The invention is especially useful for detection of monoepitopic and polyepitopic antigens and antibodies associated with pathologies, as well as physiological compounds and drugs.

The assay devices of the invention are particularly well suited for use in drug screening assays and for diagnostic testing of organisms. In the former respect, a five drug panel of assay tests is recommended by the National Institute on Drug Abuse (NIDA), which includes tests for tetrahydrocannabinol and other marijuana metabolites, cocaine metabolites, opiate metabolites, phencyclidine (PCP, Angel Dust), and amphetamines. For a more extensive substance abuse testing panel, the choice of analytes tested can include marijuana metabolites; tetrahydrocannabinol and other marijuana metabolites, cocaine metabolites, opiate metabolites, phencyclidine (PCP, Angel Dust), amphetamines, barbiturates, benzodiazepines, methaqualone, and propoxyphene. The analyte test strips for drug tests preferably have the sensitivity equal to the cutoffs recommended by Substance Abuse Mental Health Service Administration (SAMSHA) and NIDA, which most employers use. Binders and reagents for use in constructing analyte test strips for use in detecting drugs of abuse are well-known in the art and will not be described in detail here; however, representative sources of such materials are described in the Examples below.

The method of the invention is performed by applying analyte sample to analyte test strips by immersion (dipstick forms of the device; e.g., as shown in FIG. 2 and FIG. 3) or by applying the sample dropwise through slot 221 in cap 220 (FIG. 4; representing cassette forms of the device). After waiting a predetermined time, such as from about 15 seconds to about 60 seconds, test results are viewed through window 111 or 211 (FIGS. 2 and 4), either visually or by an instrument. A color change in test zone 112 or 212 (FIGS. 2 and 4) indicates the presence or concentration of analyte in the sample. When no band appears in test zones, or if the control band is neither distinct nor fully formed, the assay is regarded as incompetent to indicate the presence or absence of analyte in the test samples and may be performed again. In addition, the assay can be made quantitative by employing spectrophotometric or colorimetric techniques, as opposed to visual techniques, in order to more reliably and more accurately measure the degree of color transition, and therefore more accurately measure the concentration of analyte in the test sample.

For use of devices including the sample integrity monitoring system of the invention, a detectable signal, preferably a visually detectable signal, will appear on surface 300A of integrity determinant pad 300 (FIG. 1 and FIG. 2). In general, such detectable signal will be provided by interaction (e.g., binding) between determinants incorporated in integrity determinant pad 300 (so as to be detectable from surface 300A thereof) and specific adulterants present in the analyte sample fluid, thereby producing detectable changes in the fluid, such as an increase or reduction in pH.

G. Kits

The invention provides a kit useful for the detection of analytes of interest, having a carrier compartmentalized to receive one or more containers holding the multianalyte assay device of the invention or parts thereof. Preferably, the multianalyte assay device is part of a kit which may be composed of the device, instructions for its use, a sample collection cup, a capillary device for measuring test sample, a pipette for introduction of sample to the device, and a desiccant packet.

Desiccant provides low humidity conditions necessary for preservation of reagents during the shelf life of the device. Alternatively, a desiccant tablet or a desiccant packet may be included in an air-tight protective pouch with the device. Instructions for use of the multianalyte assay device may be printed onto the cover or onto the packaging of the multianalyte assay device or may be printed in literature to be packaged with the multianalyte assay device. The kit may additionally include an attached temperature strip, lids for the specimen cup, and the literature. Components of such a kit for use in performing an assay procedure (e.g., excluding printed instructions) are preferably to be sealed in one or more air-tight packages, such as foil packets.

The following examples are provided to illustrate a use for the invention and do not limit its scope. Unless otherwise noted, all terms and abbreviations used in the examples are standard in the art.

EXAMPLE 1

Assay for Six Drugs of Abuse

Six chromatographic strips for detecting drugs of abuse (methamphetamine, opiates/morphine, marijuana/tetrahydrocannabinol, amphetamine, cocaine/benzoylecgonine, benzodiazepine) each of a size of 5 mm×73 mm were placed in slots of the device of the invention as shown in FIG. 2. Each strip consisted of a colloidal gold-labeled antibody (specific to the target drug) incorporated into the upstream end of the strip (tracer zone) in the middle of a 30 mm fiberglass matrix, and an antigen-BSA binder immobilized in the center (binder zone) of a 22 mm nitrocellulose membrane lying downstream of, and in fluid communication with, the fiberglass matrix (wherein the antigen is either the drug of interest or an analog thereof having the same immunogenicity). Downstream to the nitrocellulose membrane was a 26 mm long filter paper. The matrix, membrane and filter paper were attached on a vinyl sheet so each was in fluid communication, by overlapping 2 mm of each of their ends.

15 drops (0.7 ml each) of analyte sample (human urine) were applied to the sample port. Results were read after 10 minutes. The presence or absence of a pink-rose color band in the binder zone indicated negative or positive results for the presence of each drug of interest in the analyte sample.

For comparison, additional aliquots of the analyte samples were separately tested for the presence of the same drugs of abuse by a commercial assay (Syva EMIT EIA II). The second panel of test results correlated with the results obtained according to the invention.

For use in determining whether the analyte samples were adulterated in any way, signals visually observable in the sample integrity monitoring system would be compared to standards such as a color chart for pH in normal, unusually acidic or unusually alkaline urine, and/or similar charts supplying information about normal or abnormal results for other parameters as described elsewhere above.

Although the invention has been described with reference to the presently preferred embodiment, it should be understood that various modifications can be made without departing from the spirit of the invention. Accordingly, the invention is limited only by the following claims.

What is claimed is:

1. A device for use in determining whether the integrity of a fluid analyte sample has been compromised and for contemporaneously assaying the sample for the presence or absence of multiple analytes, the device comprising:

(A) a base having adjacent slots therein of sufficient length for insertion of an analyte test strip therein, wherein each slot is defined by (a) a floor, (b) raised walls depending upwardly from the floor to separate each adjacent slot from the next, and (c) at least one open end;

(B) a multiplicity of analyte test strips having an upstream and a downstream end, wherein each analyte test strip occupies a separate slot of the base so the upstream end of each analyte test strip protrudes out of the open end of each slot for application of the fluid analyte sample;

(C) a sample integrity monitoring system, the system comprising:

(a) a carrier membrane which lies parallel with and underlies each analyte test strip;

(b) a sample integrity determinant pad in fluid communication with the carrier membrane; and, (c) determinants incorporated into the integrity determinant pad, which determinants provide a detectable signal for a parameter indicative of the condition of the fluid;

wherein neither the carrier membrane nor the integrity determinant pad are in appreciable fluid communication with any of the analyte test strips.

2. The device according to claim 1 further comprising a cap for insertion over the protruding ends of the analyte test strips.

3. The device according to claim 1, wherein the carrier membrane of the sample integrity monitoring system lies partially beneath and in a slot with the analyte test strip; wherein further the carrier membrane extends in length beyond the downstream end of the analyte test strip to define a platform for the sample integrity monitoring pad; and, wherein further the sample integrity determinant pad rests on top of such platform.

4. The device according to claim 1, wherein the carrier membrane of the sample integrity monitoring system lies partially above and in a slot with the analyte test strip; wherein further the carrier membrane extends in length beyond the downstream end of the analyte test strip to define a platform for the sample integrity monitoring pad; and, wherein further the sample integrity determinant pad rests below such platform.

5. The device according to claim 1 wherein the carrier membrane of the sample integrity monitoring system occupies a different slot than the slot occupied by the analyte test strip.

6. The device according to claim 1, further comprising a multiplicity of analyte test strips which occupy separate slots of the base, wherein each analyte test strip has a test zone therein and each test zone contains a binder specific for a different analyte.

7. The device according to claim 3, further comprising a multiplicity of analyte test strips which occupy separate slots of the base, wherein each analyte test strip has a test zone therein and each test zone contains a binder specific for a different analyte.

8. The device according to claim 4, further comprising a multiplicity of analyte test strips which occupy separate slots of the base, wherein each analyte test strip has a test zone therein and each test zone contains a binder specific for a different analyte.

9. The device according to claim 5, further comprising a multiplicity of analyte test strips which occupy separate slots of the base, wherein each analyte test strip has a test zone therein and each test zone contains a binder specific for a different analyte.

10. The device according to any one of claims 6 through 9, wherein each binder is specific for a different drug of abuse.

11. The device according to any one of claims 6 through 9, wherein the device includes a cover overlying the slots of the base and each test zone of the analyte test strips is visible through a transparent window through the cover.

12. The device according to any one of claims 6 through 9, wherein each analyte test strip further comprises a label downstream of the test zone, which label identifies the analyte for which the binder is specific.

13. The device according to any one of claims 6 through 9, wherein each binder is specific for a different drug of abuse selected from the group of drugs of abuse consisting of methamphetamine, opiates/morphine, marijuana/tetrahydrocannabinol, amphetamine, cocaine/benzoylecgonine, methadone, PCP, barbiturate, trichloroacetic acid and benzodiazepine.

14. The device according to claim 1, wherein the parameter indicative of the condition of the fluid analyte sample evaluated is selected from the group consisting of pH, osmolality, albumin level, creatinine level, glutaraldehyde level and nitrite level.

15. The device according to claim 1, wherein fluid communication between the sample integrity monitoring system and each analyte test strip is prevented by a fluid barrier disposed on the carrier membrane between the downstream end of each analyte test strip and the integrity determinant pad.

16. The device according to claim 15, wherein the fluid barrier is a hydrophobic film.

17. The device according to claim 15, wherein the fluid barrier is a physical gap between the downstream end of each analyte test strip and the integrity determinant pad.

18. The device according to claim 15, wherein the fluid barrier is an absorbent pad.

19. The device according to claim 18, wherein a hydrophobic material is incorporated into the absorbent pad.

20. A method for use in determining whether the integrity of a fluid analyte sample has been compromised and for contemporaneously assaying the sample for the presence or absence of multiple analytes, the method comprising:
(A) immersing the protruding ends of the analyte test strips of the device of claim 1 into the fluid analyte sample;
(B) reading the assay results visible on the analyte test strips; and,
(C) reading the results obtained by the sample integrity monitoring system;
wherein a detectable signal on an analyte test strip is indicative of the presence or absence of the analyte being screened for in said sample by said analyte test strip; and wherein a detectable signal on the sample integrity monitoring system is indicative of the presence or absence of adulteration in said sample.

21. The method according to claim 20, further comprising the step A', wherein the sample in a closed specimen collection cup having a separation device therein, the separation device comprising a V-shaped trough transversing a ring placable in the cup, wherein sample separation is accomplished by inverting the specimen collection cup to allow fluid analyte sample to flow into the collection chamber of the separator device; and wherein further step A' is performed by immersing the protruding ends of the analyte test strips into the fluid collected in the chamber.

22. The method according to claim 20, wherein the parameter indicative of the condition of the analyte sample fluid evaluated is selected from the group consisting of pH, osmolality, albumin level, creatinine level, glutaraldehye level and nitrite level.

* * * * *